(12) United States Patent
Dardzinski et al.

(10) Patent No.: US 11,504,153 B1
(45) Date of Patent: Nov. 22, 2022

(54) BIOCYL PLAQUE EXTRACTOR

(71) Applicant: Most Cardio LLC, Salem, MA (US)

(72) Inventors: Victor Dardzinski, Saugus, MA (US); Pavel Menn, Salem, MA (US)

(73) Assignee: MOST CARDIO, LLC, Salem, MA (US)

( * ) Notice: Subject to any disclaimer, the term of this patent is extended or adjusted under 35 U.S.C. 154(b) by 0 days.

(21) Appl. No.: 17/826,210

(22) Filed: May 27, 2022

(51) Int. Cl.
*A61B 17/3207* (2006.01)
*A61B 17/32* (2006.01)

(52) U.S. Cl.
CPC .......... *A61B 17/320758* (2013.01); *A61B 2017/320052* (2013.01); *A61B 2017/320064* (2013.01); *A61B 2017/320716* (2013.01); *A61B 2017/320766* (2013.01)

(58) Field of Classification Search
CPC ...... A61B 17/32002; A61B 17/320725; A61B 17/320758; A61B 2017/00685; A61B 2017/320024; A61B 2017/320032; A61B 2017/320052; A61B 2017/320064; A61B 2017/320716; A61B 2017/320766; A61B 2017/320775
See application file for complete search history.

(56) References Cited

U.S. PATENT DOCUMENTS

| | | | | |
|---|---|---|---|---|
| 5,899,915 | A * | 5/1999 | Saadat | A61B 17/32002 604/22 |
| 9,314,263 | B2 * | 4/2016 | Escudero | A61B 17/320758 |
| 2007/0239182 | A1 * | 10/2007 | Glines | A61B 17/320758 606/159 |
| 2008/0045986 | A1 * | 2/2008 | To | A61M 25/0152 606/159 |
| 2012/0109171 | A1 * | 5/2012 | Zeroni | A61B 17/320758 606/159 |
| 2014/0222048 | A1 * | 8/2014 | Ladd | A61B 17/3207 606/159 |
| 2017/0000518 | A1 * | 1/2017 | Smith | A61B 17/320758 |

* cited by examiner

*Primary Examiner* — Elizabeth Houston
*Assistant Examiner* — Lindsey Bachman
(74) *Attorney, Agent, or Firm* — Daniel N. Smith

(57) ABSTRACT

An improved plaque extractor for shaving, scooping, cutting, and emulsifying accumulated plaque from blood vessels into fine particles, and removing the particles from blood vessel walls without cutting or permanently stretching the walls, and without substantially blocking the blood flow through the vessel during plaque removal operation. The plaque extractor includes an extractor guide and an internal auger, in which both are rotating and moving axially inside the vessel to engage the occlusive material. The operation of the device does not substantially disrupt blood pressure within the blood vessel.

20 Claims, 16 Drawing Sheets

BIOCYL PLAQUE EXTRACTOR

FIELD OF THE INVENTION

This invention relates to an improved blood vessel plaque extractor for shaving, scooping, cutting, and emulsifying accumulated plaque from blood vessel walls into small particles, without cutting or permanently stretching the walls, and without substantially blocking the blood flow through the vessel during plaque removal operation.

BACKGROUND OF INVENTION

Atherosclerosis is a form of arteriosclerosis in which plaque accumulates in an arterial vessel and the artery wall thickens as a result of invasion and accumulation of white blood cells on the inner artery vessel walls. These plaque accumulations contain both living, active WBCs (producing inflammation) and remnants of dead cells, including cholesterol and triglycerides. The remnants eventually include calcium and other crystallized materials, to form plaque. The plaque reduces the elasticity of the artery vessel walls. It is commonly referred to as a "hardening" or furring of the arteries.

Over time these plaques can become large enough to reduce or occlude blood flow through the vessels, leading to symptoms of low blood flow. To treat this disease blood flow must be restored through the vessel, by removing or reducing the size of these plaques.

Various types of plaque removal devices and techniques have been used to remove unwanted plaque from blood vessels to open the vessel and improve blood flow. For example, atherectomy catheters and devices are intravascular devices that mechanically remove plaque from the artery vessel walls.

However, atherectomy catheters and devices often undesirably cut, perforate, tear and stretch the vessel, causing scar formation. Such scar tissue causes inflammation, stenosis and blocks flow in the vessel and often needs to be removed. Furthermore, atherectomy catheters often run at high speeds causing temperature and causing damage to the vessels. Finally, atherectomy catheters block arterial blood flow completely during plaque removal, resulting in high vessel blood pressure, and posing a danger to the patient.

It is therefore desirable to provide an improved device and method for removing plaque from artery vessel walls, without cutting or permanently stretching the walls, and without reducing blood flow or increasing blood pressure during operation.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a device configured to remove occlusive material from a vessel, comprising: a catheter with a hollow elongated lumen, a proximal opening, and a distal opening; a plaque extractor guide on the distal opening of the catheter, wherein the plaque extractor guide comprises a substantially cylindrical shape with an exterior surface; wherein the plaque extractor guide comprises a first channel traversing subtantially one half of the cylindrical shape, with a proximal opening and a distal opening, wherein the first channel is substantially crescent shaped, further wherein the plaque extractor guide comprises a second channel traversing subtantially the other half of the cylindrical shape with a proximal opening and a distal opening, wherein the second channel is substantially circular, further wherein the proximal end of the second channel is substantially aligned with the distal opening of the catheter; wherein the distal end of the second channel of the plaque extractor guide comprises a slot and a scoop, wherein the scoop comprises a substantially smooth, curved surface extending outward, and a distal blunt edge, and the slot comprises a substantially smooth, curved surface extending inward; a substantially cylindrical cutting auger contained with the second channel of the plaque extractor guide, wherein the cutting auger comprises a proximal end and a distal end, wherein the proximal end of the cutting auger is substantially aligned with the distal opening of the catheter; at least two occlusive material cutting edges on a distal end of the cutting auger extending outwardly from the distal opening of the second channel of the plaque extractor guide; wherein the plaque extractor guide and the cutting auger are configured to each independently rotate in opposite directions during plaque extraction and move axially inside the vessel to engage the occlusive material; wherein the plaque extractor guide rotates around its center axis, and the cutting auger and catheter rotate in an eccentric rotation and move axially in an eccentric path within the vessel; wherein the slot and the scoop of the plaque extractor guide shaves and scoops the occlusive material located outside the eccentric path of the eccentrically rotating cutter into the side cutting edges of the cutting auger for emulsification into reduced particles such that the movement of the slot and the scoop of the plaque extractor guide does not pierce or cut the vessel wall; wherein occlusive material located within the eccentric path of the eccentrically rotating cutter is emulsified into reduced particles by the distal cutting edges; wherein the cutting auger is configured to not contact the vessel wall; wherein the mixture of emulsified occlusive material and blood flows in a proximal direction into the catheter lumen through the cutting auger; and wherein the remainder of the blood flowing distally through the substantially crescent shaped first channel of the plaque extractor guide, continues to flow downstream.

The subject invention discloses a device configured to remove occlusive material from a vessel, comprising: a catheter with a hollow elongated lumen, a proximal opening, and a distal opening; a plaque extractor guide on the distal opening of the catheter, wherein the plaque extractor guide comprises a substantially cylindrical shape with an exterior surface; wherein the plaque extractor guide comprises a first internal channel with a proximal opening and a distal opening; further wherein the plaque extractor guide comprises a second internal channel with a proximal opening and a distal opening, wherein the proximal end of the second channel is substantially aligned with the distal opening of the catheter; wherein the distal end of the second channel of the plaque extractor guide comprises a slot and a scoop, wherein the scoop comprises a substantially smooth, curved surface extending outward, and a distal blunt edge, and the slot comprises a substantially smooth, curved surface extending inward; a substantially cylindrical cutting auger contained within the second channel of the plaque extractor guide, wherein the cutting auger comprises a proximal end and a distal end, wherein the proximal end of the cutting auger is substantially aligned with the distal opening of the catheter; at least two occlusive material cutting edges on the distal end of the cutting auger extending outwardly from the distal opening of the second channel of the plaque extractor guide; wherein the plaque extractor guide and the cutting auger are configured to each independently rotate in opposite directions during plaque extraction and move axially inside the vessel to engage the occlusive material; wherein the plaque extractor guide rotates around its center axis, and the cutting auger and catheter rotate in an eccentric rotation and move axially in an eccentric path within the vessel; wherein the slot and the scoop of the plaque extractor guide shaves and scoops the occlusive material located outside the eccentric path of the eccentrically rotating cutter into the side cutting edges of the cutting auger for emulsification into reduced particles such that the movement of the slot and the scoop of the plaque extractor guide does not pierce or cut the vessel wall; wherein occlusive material located within the eccentric path of the eccentrically rotating cutter is emulsified into reduced particles by the distal cutting edges; wherein the cutting auger is configured to not contact the vessel wall; wherein the mixture of emulsified occlusive material and blood flows in a proximal direction into the catheter lumen through the cutting auger; and wherein the remainder of the blood flowing distally through the substantially crescent shaped first channel of the plaque extractor guide, continues to flow downstream.

The subject invention further discloses a device configured to remove occlusive plaque from a vessel, comprising: a catheter with a hollow elongated lumen, a proximal opening, and a distal opening; a plaque extractor shield on the distal opening of the catheter, wherein the plaque extractor shield comprises a substantially cylindrical shape with an exterior surface; wherein the plaque extractor shield comprises a first channel traversing subtantially one half of the cylindrical shape, with a proximal opening and a distal opening, wherein the first channel is substantially crescentoid shaped, further wherein the plaque extractor shield comprises a second channel traversing subtantially the other half of the cylindrical shape with a proximal opening and a distal opening, wherein the second channel is substantially circular, further wherein the proximal end of the second channel is substantially aligned with the distal opening of the catheter; wherein the distal end of the second channel of the plaque extractor shield comprises a slot and a scoop, wherein the scoop comprises a substantially smooth, curved surface extending outward, and a distal blunt edge, and the slot comprises a substantially smooth, curved surface extending inward; a substantially cylindrical plaque emulsifier contained within the second channel of the plaque extractor shield, wherein the plaque emulsifier comprises a proximal end and a distal end, wherein the proximal end of the plaque emulsifier is substantially aligned with the distal opening of the catheter; at least two occlusive plaque cutting edges on the distal end of the plaque emulsifier extending outwardly from the distal opening of the second channel of the plaque extractor shield; wherein the plaque extractor shield and the plaque emulsifier are configured to each independently rotate in opposite directions during plaque extraction and move axially inside the vessel to engage the occlusive plaque; wherein the plaque extractor shield rotates around its center axis, and the plaque emulsifier and catheter rotate in an eccentric rotation and move axially in an eccentric path within the vessel; wherein the slot and the scoop of the plaque extractor shield shaves and scoops the occlusive plaque located outside the eccentric path of the eccentrically rotating cutter into the side cutting edges of the plaque emulsifier for emulsification into reduced particles such that the movement of the slot and the scoop of the plaque extractor shield does not pierce or cut the vessel wall; wherein occlusive plaque located within the eccentric path of the eccentrically rotating cutter is emulsified into reduced particles by the distal cutting edges; wherein the plaque emulsifier is configured to not contact the vessel wall; wherein the mixture of emulsified occlusive plaque and blood flows in a proximal direction into the catheter lumen through plaque emulsifier; and wherein the remainder of the blood flowing distally through the substantially crescent shaped first channel of the plaque extractor guide, continues to flow downstream.

In embodiments of the subject invention, the plaque extractor guide rotates at a rate of 20 rpm to 180 rpm.

In embodiments of the subject invention, the cutting auger rotates at a rate of 60 rpm to 5000 rpm.

In embodiments of the subject invention, the distal remaining blood flow through the first channel of the plaque extractor guide substantially maintains internal blood pressure within the vessel.

In embodiments of the subject invention, the distal remaining blood flow through the first channel of the plaque extractor guide substantially reduces any increase in internal blood pressure within the vessel due to insertion and operation of the device within the vessel.

In embodiments of the subject invention, the plaque extractor guide comprises a diameter of 1.5 to 8 millimeters.

In embodiments of the subject invention, the rotational movement of the plaque extractor guide is independent from the rotational movement of the screw cutter, wherein the plaque extractor guide and the screw cutter are locked to maintain the same relative axial positions to one another.

In embodiments of the subject invention, the cutting auger rotates at a rate faster than the plaque extractor guide.

In embodiments of the subject invention, the substantially crescent shaped first channel comprises a width of 30% to 45% of the diameter of the plaque extractor guide.

In embodiments of the subject invention, the substantially circular shaped second channel comprises a width of 30% to greater than 50% of the diameter of the plaque extractor guide.

In embodiments of the subject invention, the plaque extractor guide and the cutting auger are configured to each independently rotate in the same direction during navigation to move axially within a guide sheath, guide catheter or blood vessel while the device is being delivered to the occlusion site to minimize friction against the sheath, catheter and vessel walls.

In embodiments of the subject invention, the substantially circular shaped second channel comprises a diameter that is 50% to 150% larger than width of the substantially crescent shaped first channel on the plaque extractor guide.

In embodiments of the subject invention, the plaque extractor guide may also be referred to as a plaque extractor shield, plaque extractor guard, plaque extractor cover, plaque extractor scoop or other terms known to those skilled in the art.

In embodiments of the subject invention, the first channel of the plaque extractor guide may be substantially crescent shaped, crescentoid shaped, c-shaped, oval, circular, half-moon shaped, sickle shaped, menicus shaped, or other shapes known to those skilled in the art.

In embodiments of the subject invention, the cutting auger may also be referred to as an extraction wire, a screw auger, plaque extractor, plaque emulsifier, plaque macerator, plaque pulverizer, plaque separator, plaque remover, or other terms known to those skilled in the art.

In additional embodiments of the subject invention, the first crescent shaped channel may comprise an inflatable and deflatable balloon. In this embodiment, as the plaque extractor guide and cutting auger are being delivered to or removed from the occlusion material site, the balloon structure is deflated to minimize the overall diameter of the plaque extractor guide and allow a smaller incision on the patient and smaller diameter guide sheath or guide catheter to be used to access the occluded vessel.

In embodiments of the subject invention, the balloon structure may be inflated during plaque extraction and deflated during delivery and removal of the device to minimize the overall diameter of the extractor guide, allowing the use of a smaller diameter guide catheter to access the occluded vessel.

In embodiments of the subject invention, the cutting auger may be constructed with or without a lumen passing axially through its center axis, allowing the device to be delivered over a guide wire where applicable.

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

In embodiments of the subject invention, the term "relatively" is defined as a comparison of a property, or the proportion of a property between two components.

BRIEF DESCRIPTION OF THE DRAWINGS

Advantages of the present invention will be apparent from the following detailed description of embodiments, which description should be considered in conjunction with the accompanying drawings, in which.

DETAILED DESCRIPTION OF THE EMBODIMENTS

While several variations of the present invention have been illustrated by way of example in particular embodiments, it is apparent that further embodiments could be developed within the spirit and scope of the present invention. However, it is to be expressly understood that such modifications and adaptations are within the spirit and scope of the present invention, and are inclusive, but not limited to the following appended claims as set forth.

Figure 1:
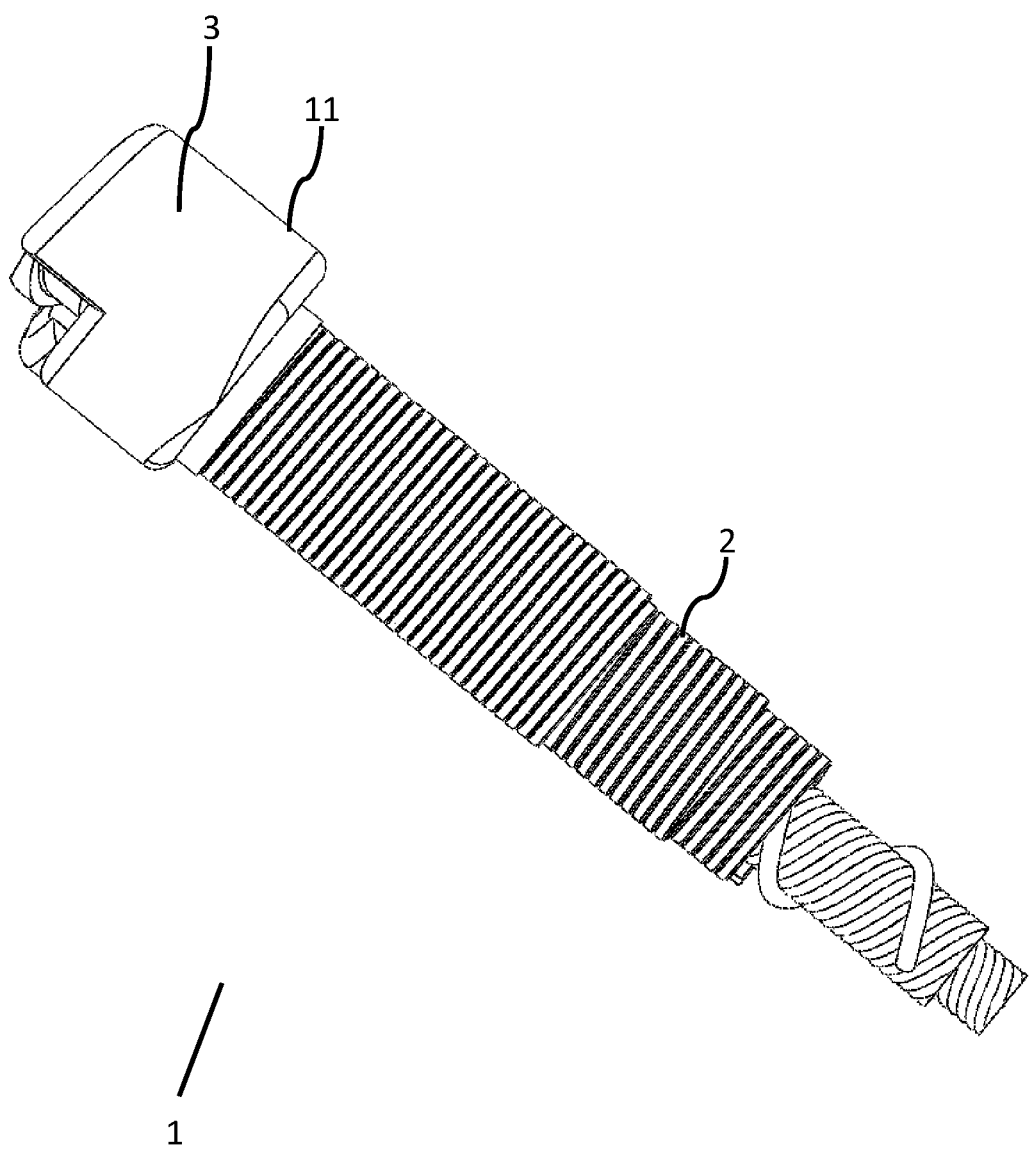
FIG. 1 Illustrates a top isometric view of a plaque extractor with a plaque extractor guide, a cutting auger, and a catheter.
Figure 2:
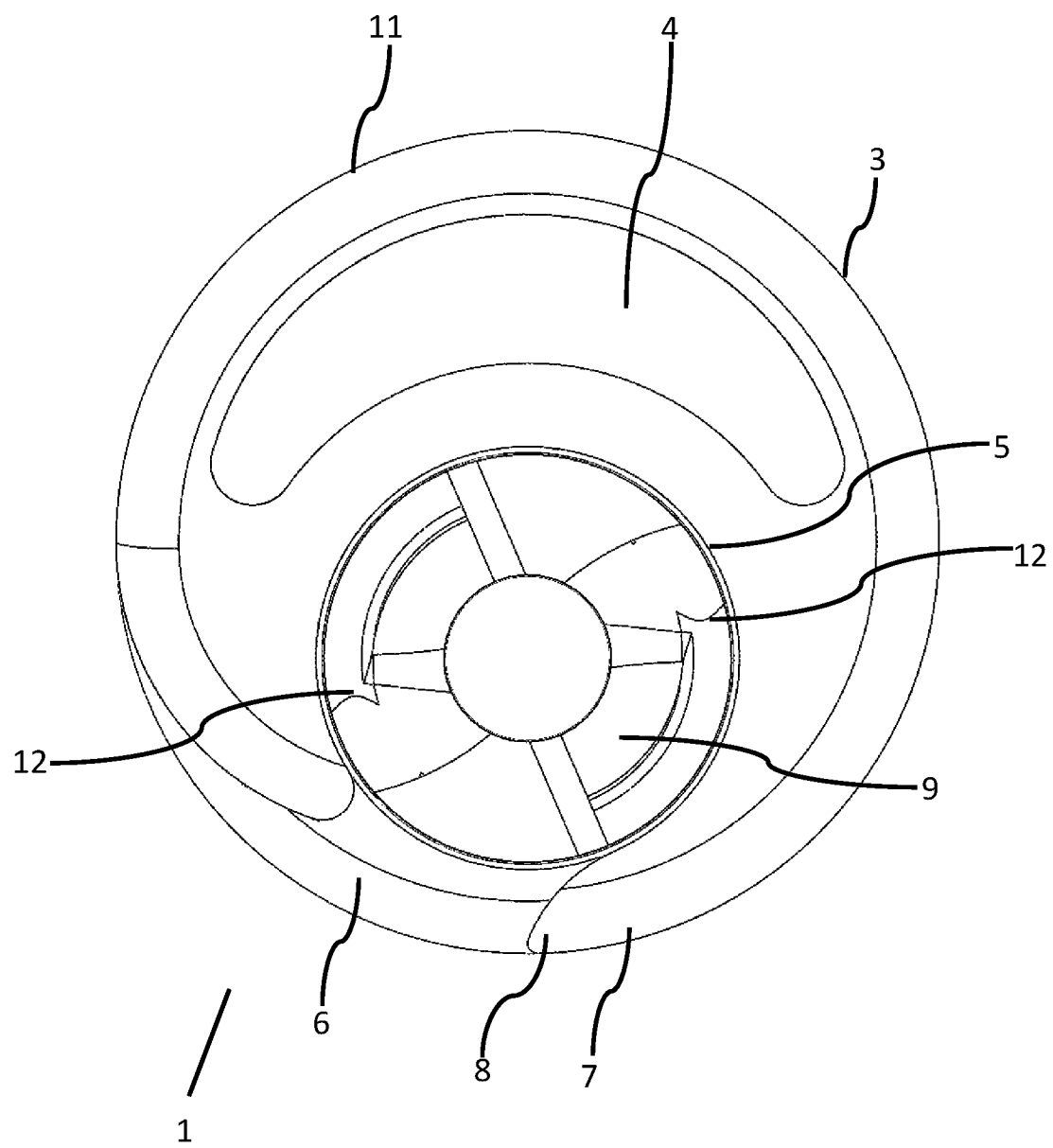
FIG. 2 Illustrates a front view of a distal end of the plaque extractor with the guide, the cutting auger, and the catheter.
Figure 3:
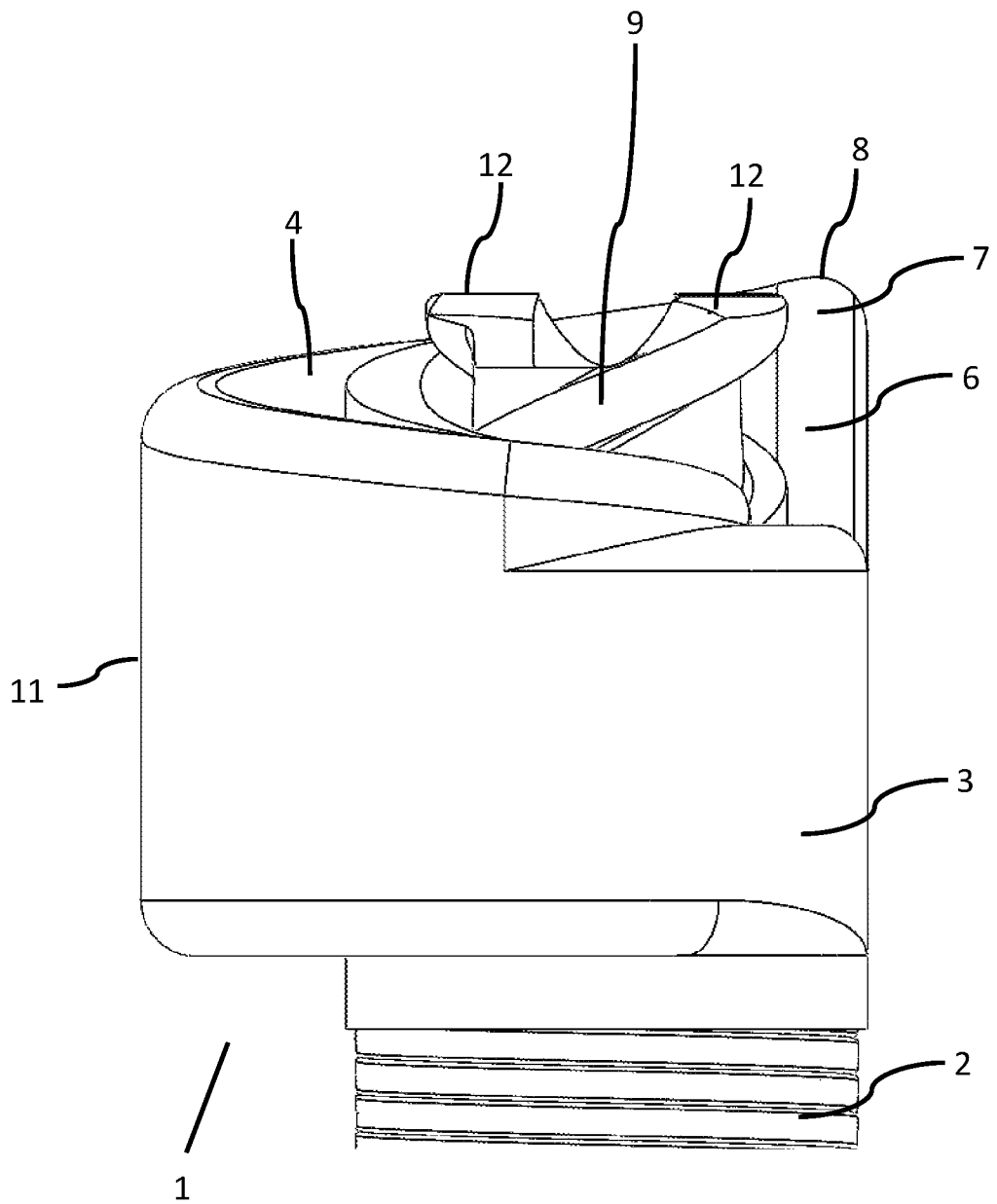
FIG. 3 Illustrates a side view of the distal end of the plaque extractor with the guide and the cutting auger.
Figure 4:
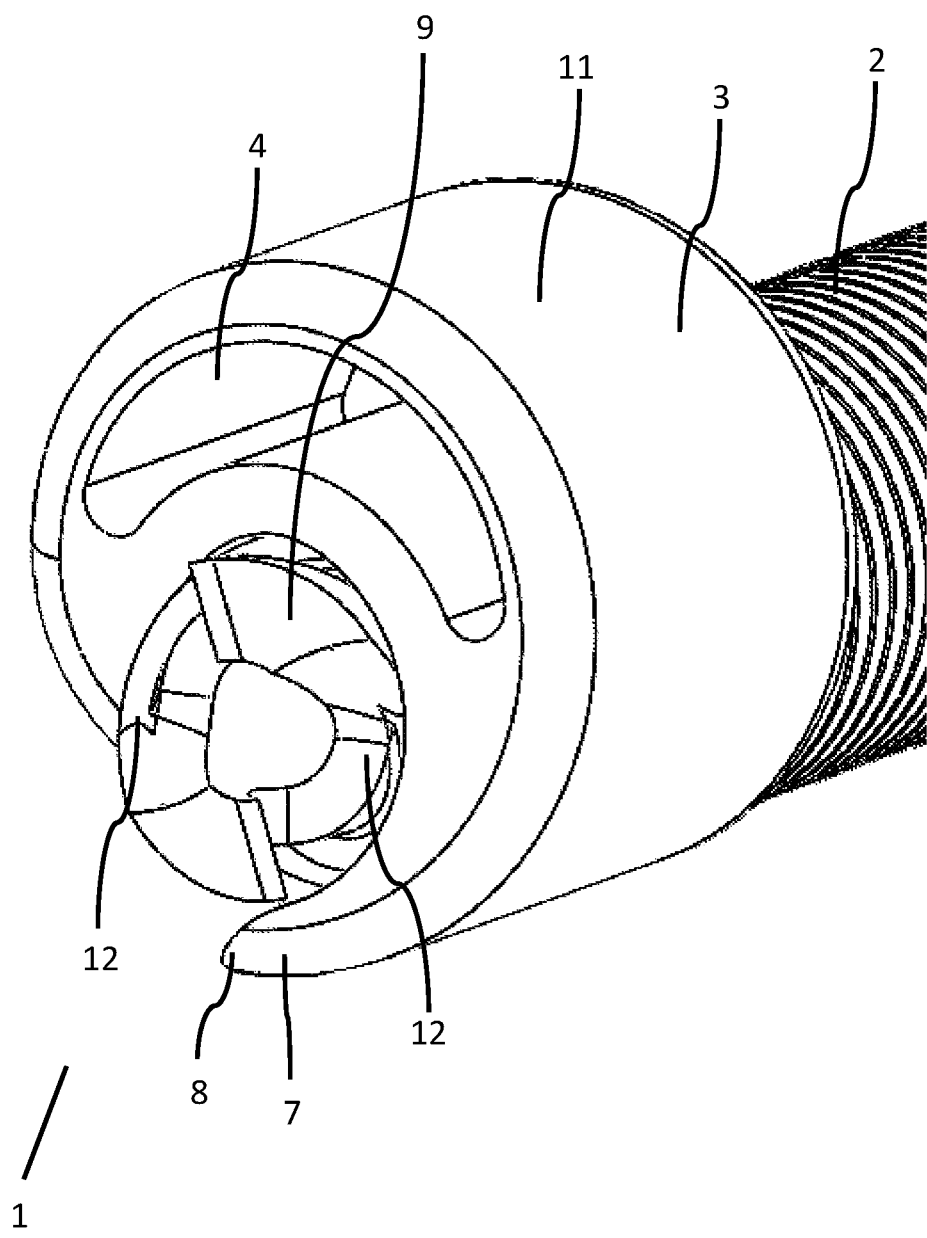
FIG. 4 Illustrates another top isometric view of the distal end of the plaque extractor with the guide and the cutting auger.
Figure 5:
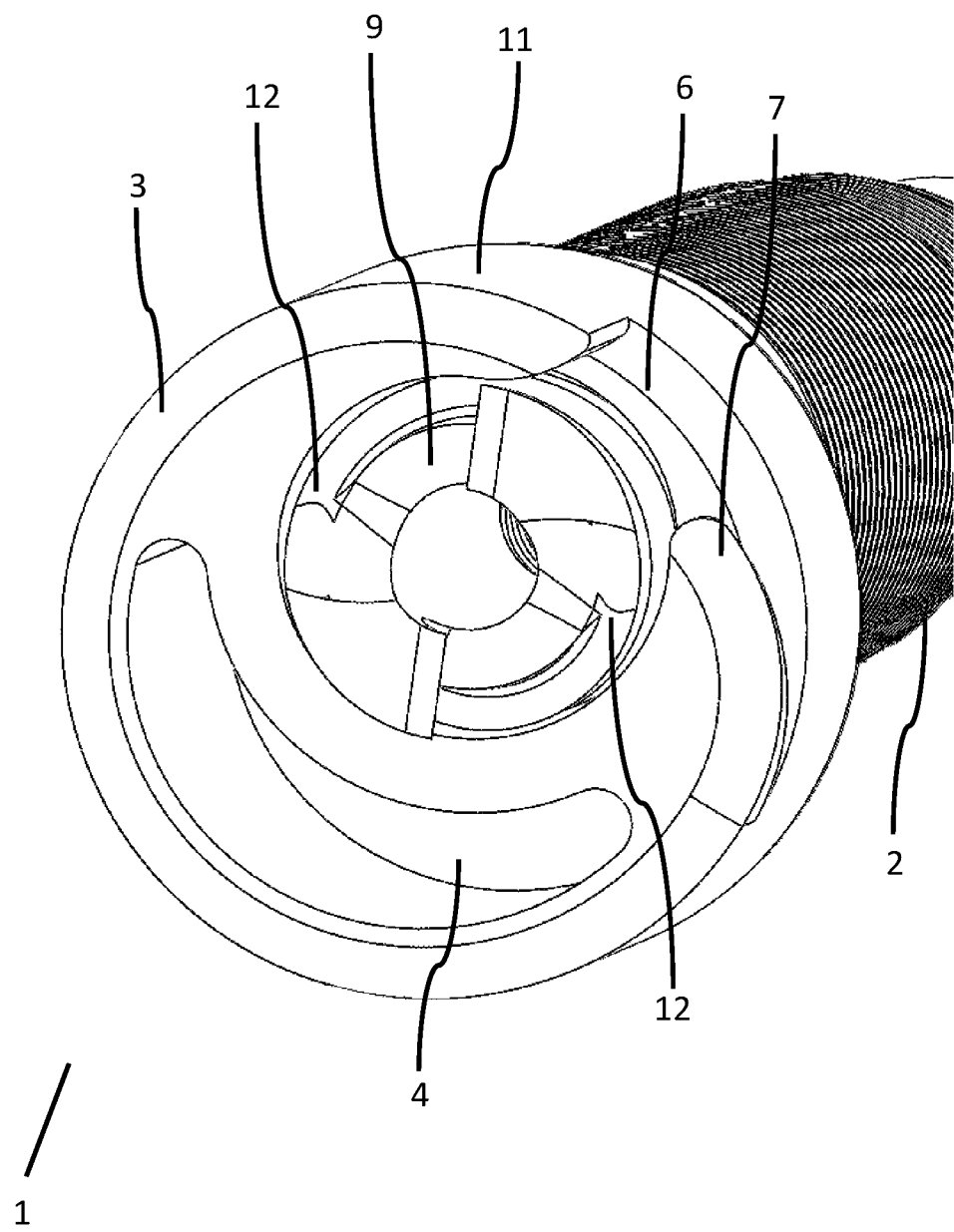
FIG. 5 Illustrates another top isometric view of the distal end of the plaque extractor with the guide and the cutting auger.
Figure 6:
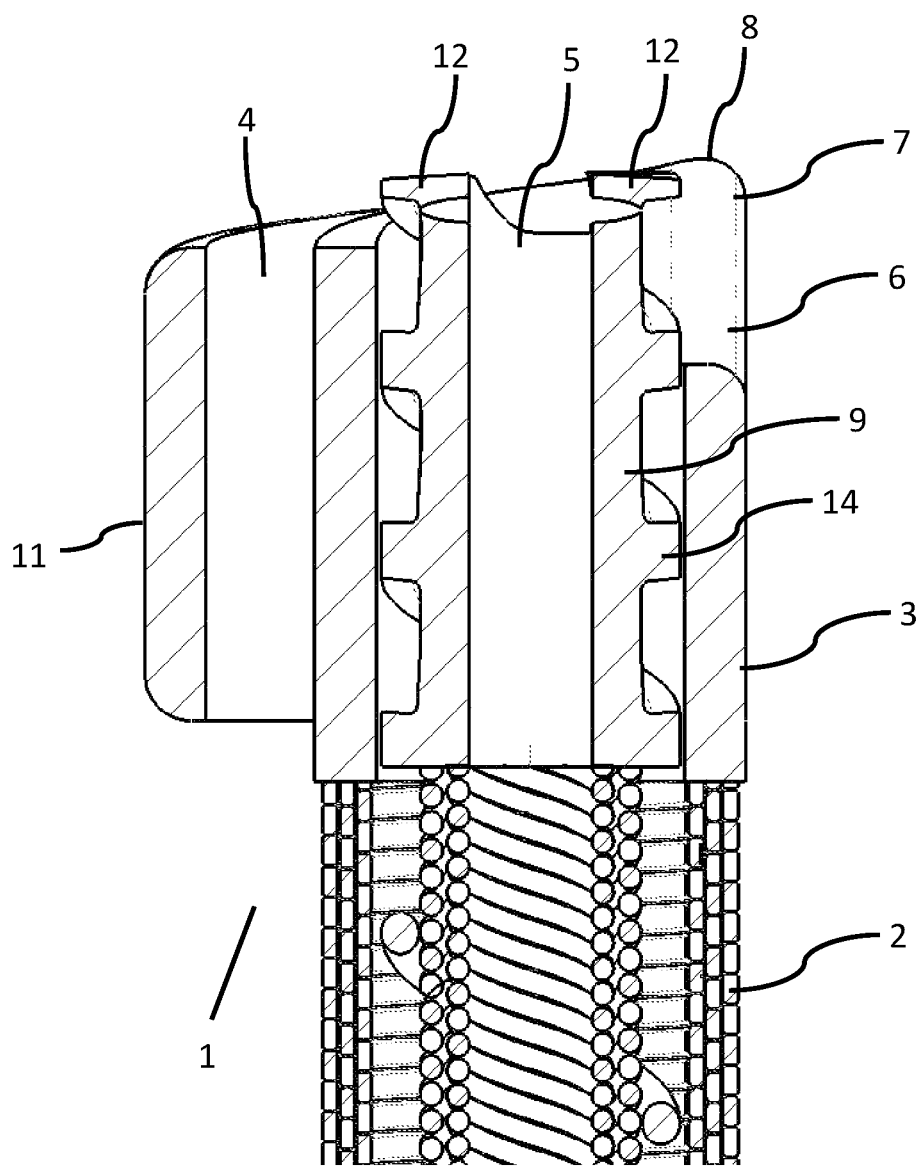
FIG. 6 Illustrates a side cross-sectional view of the distal end of the plaque extractor with the guide and the cutting auger.
Figure 7:
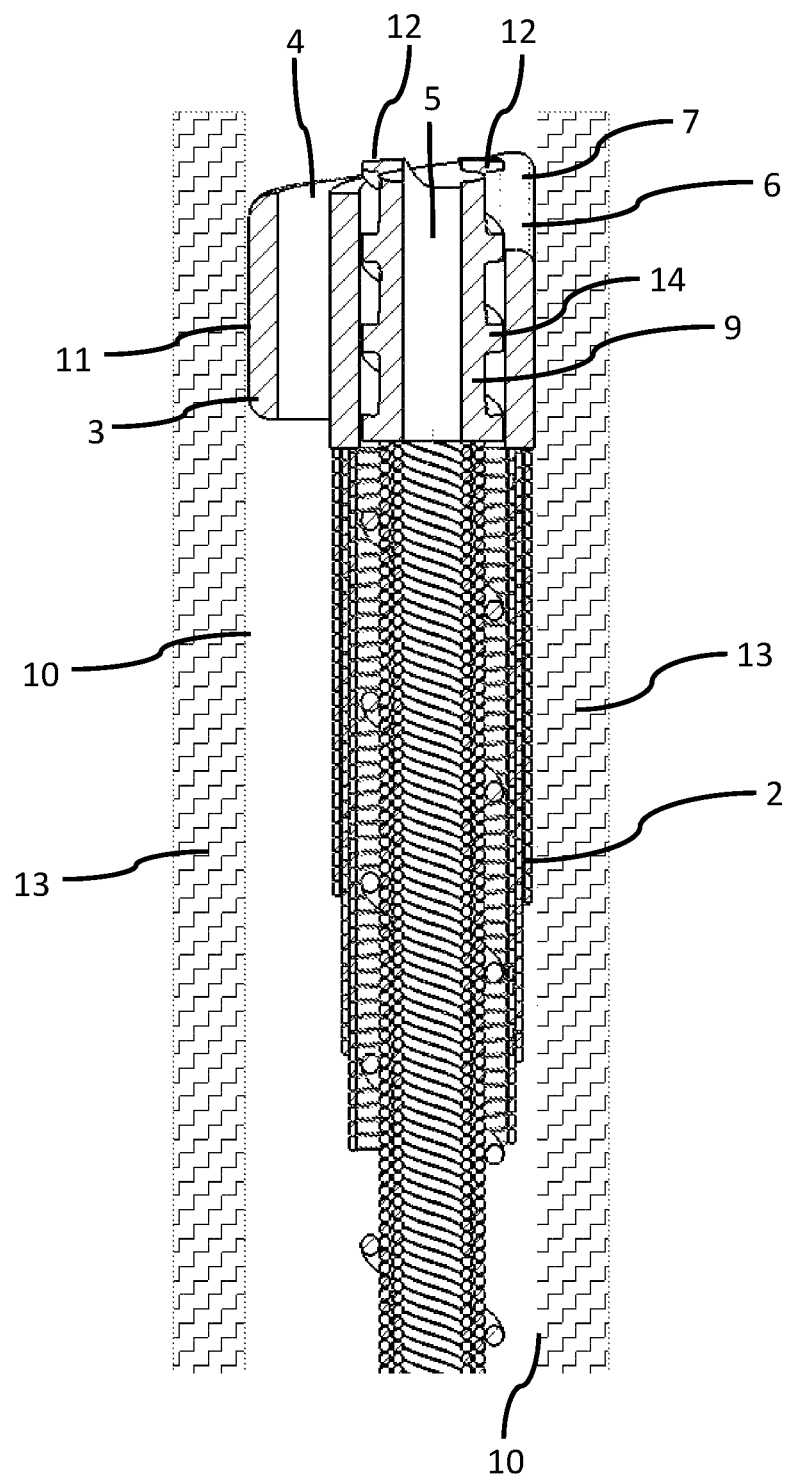
FIG. 7 Illustrates a side cross-sectional view of the distal end of the plaque extractor with the guide and the cutting auger within a vessel.
Figure 8:
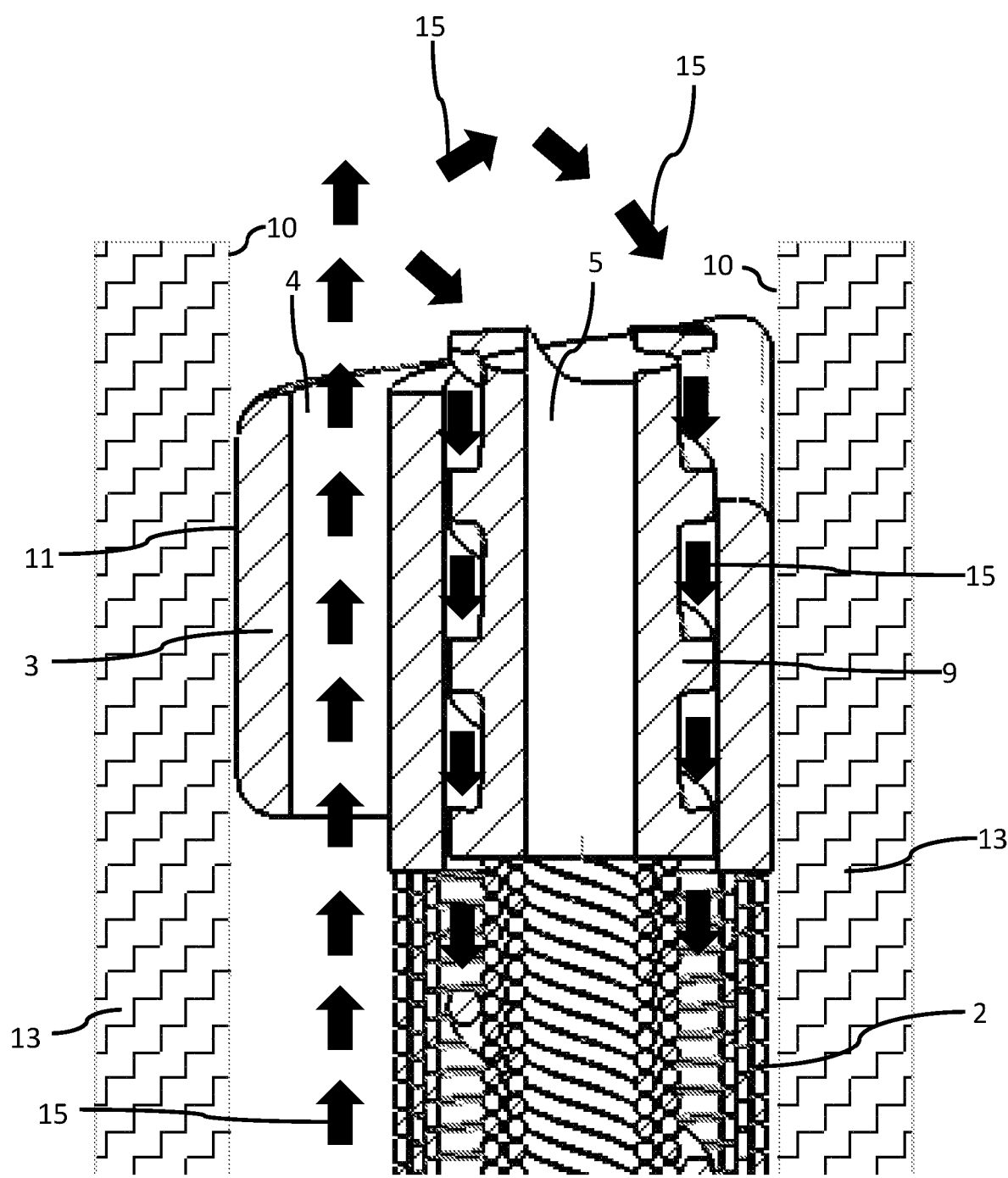
FIG. 8 Illustrates another side cross-sectional view of the distal end of the plaque extractor, with the guide and the cutting auger within a vessel, including arrows indicating blood flow.
Figure 9:
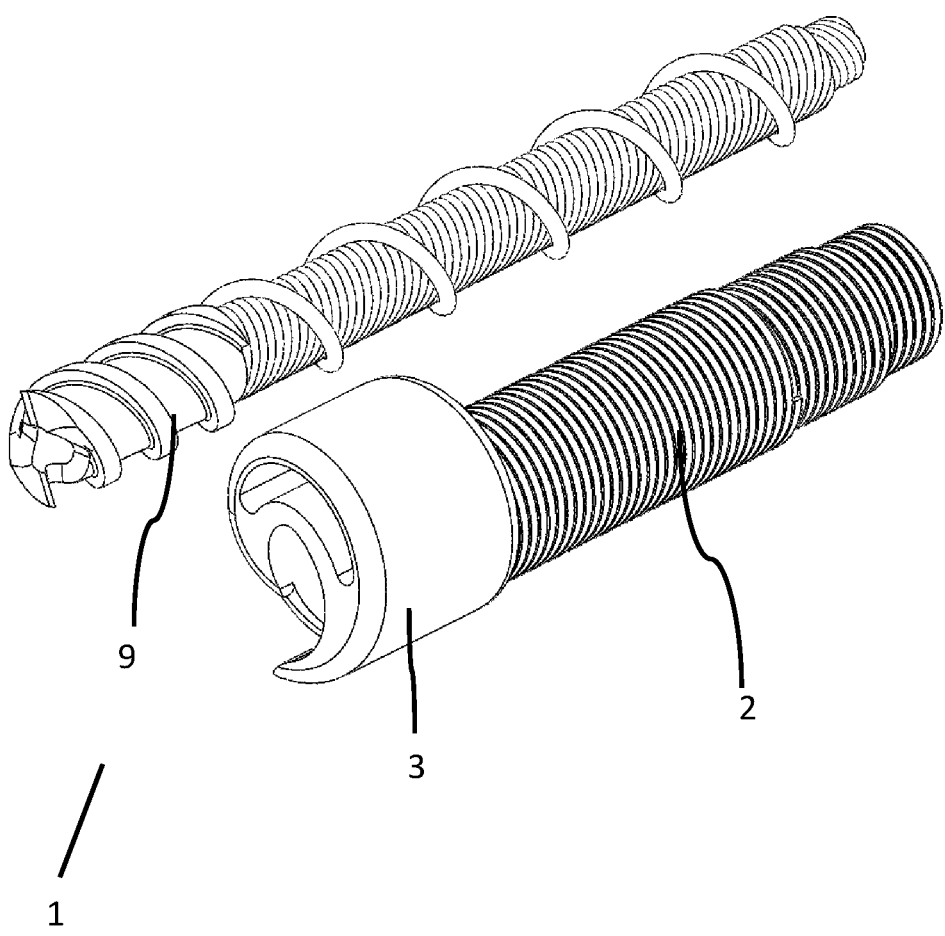
FIG. 9 Illustrates a top isometric view of the plaque extractor guide, the cutting auger, and the catheter of the subject invention.
Figure 10:
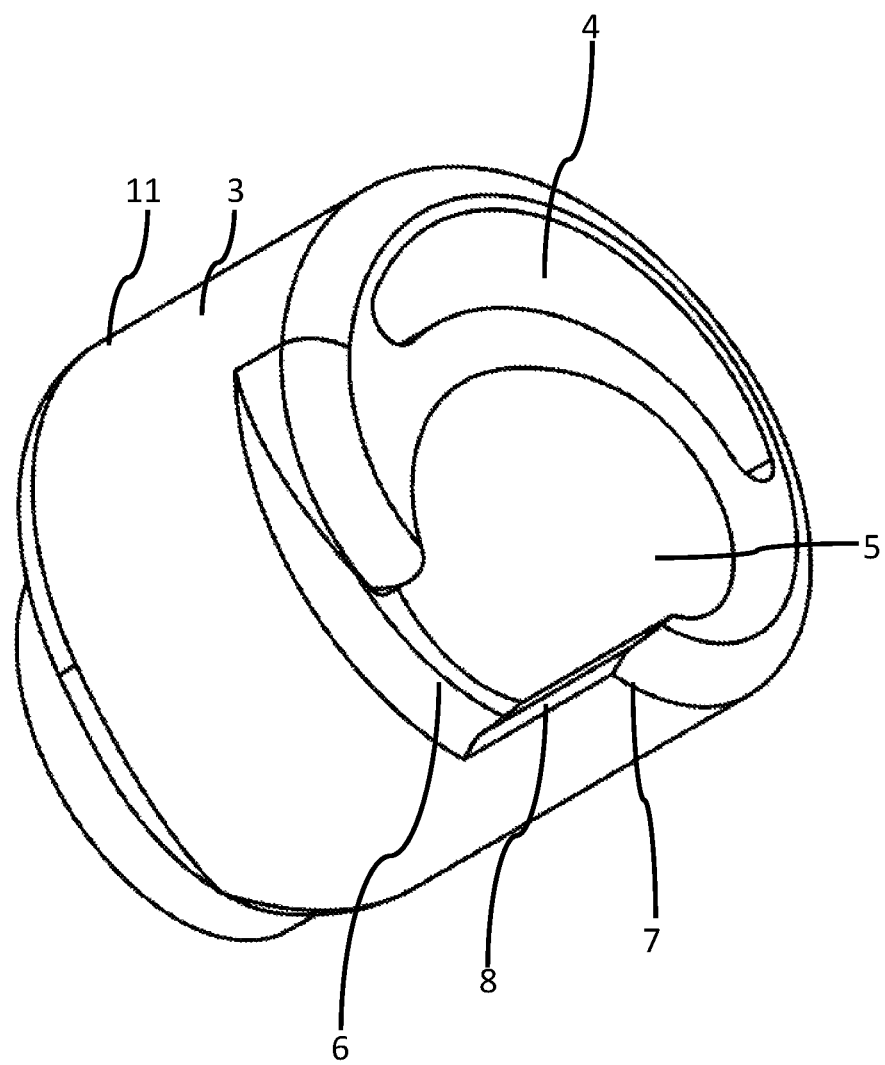
FIG. 10 Illustrates a top isometric view of the plaque extractor guide without the internal cutting auger.
Figure 11:
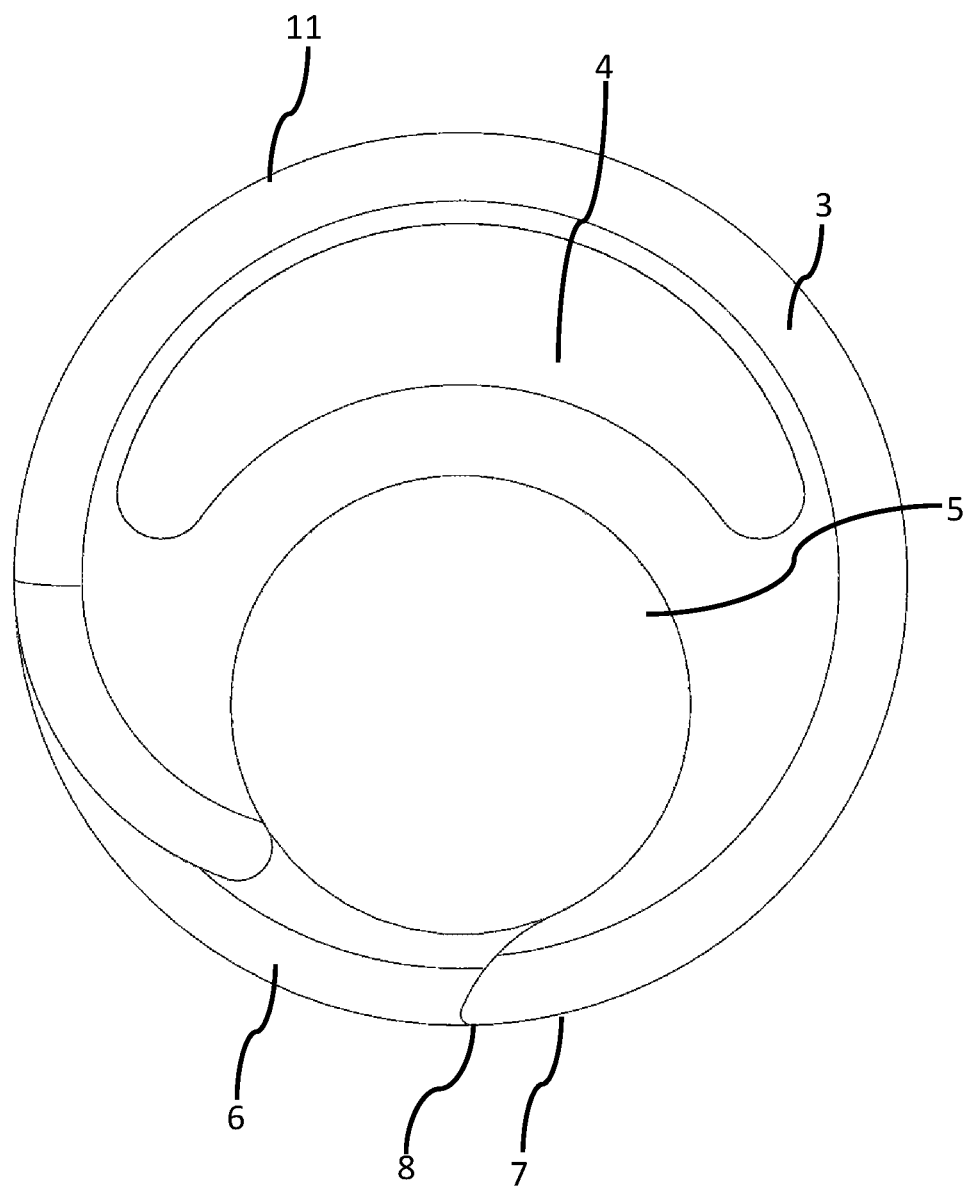
FIG. 11 Illustrates a front view of the plaque extractor guide without the internal cutting auger.
Figure 12:
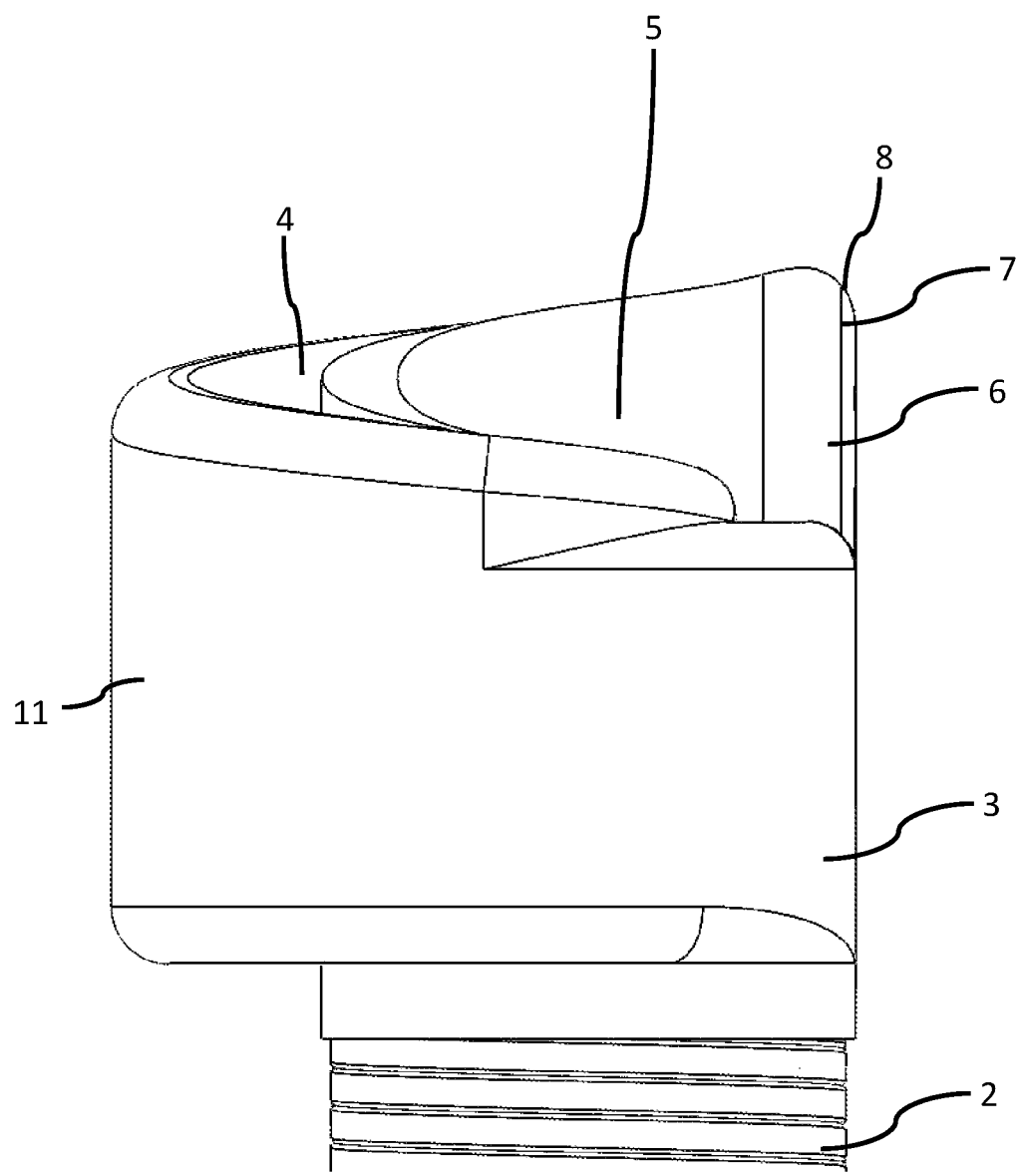
FIG. 12 Illustrates a side view of the plaque extractor guide without the internal cutting auger.
Figure 13:
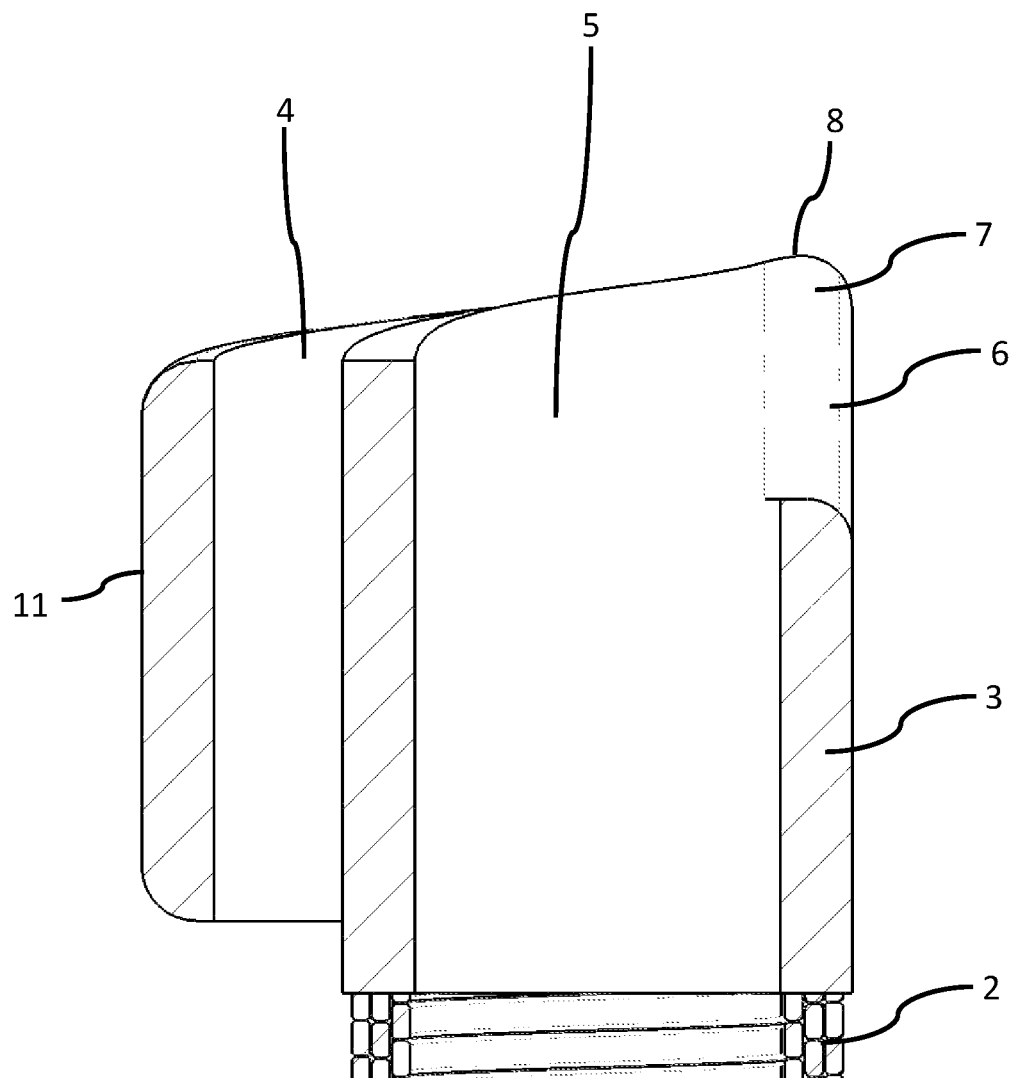
FIG. 13 Illustrates a side cross-sectional view of the plaque extractor guide without the internal cutting auger.
Figure 14:
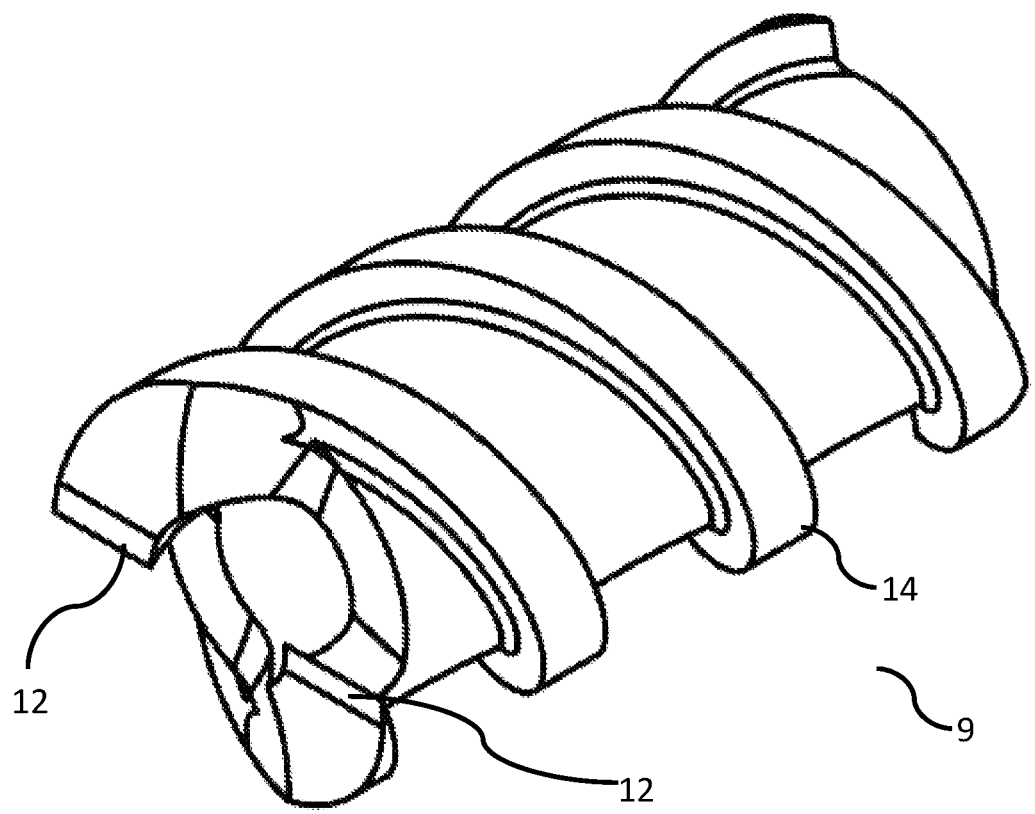
FIG. 14 Illustrates a top isometric view of the cutting auger.
Figure 15:
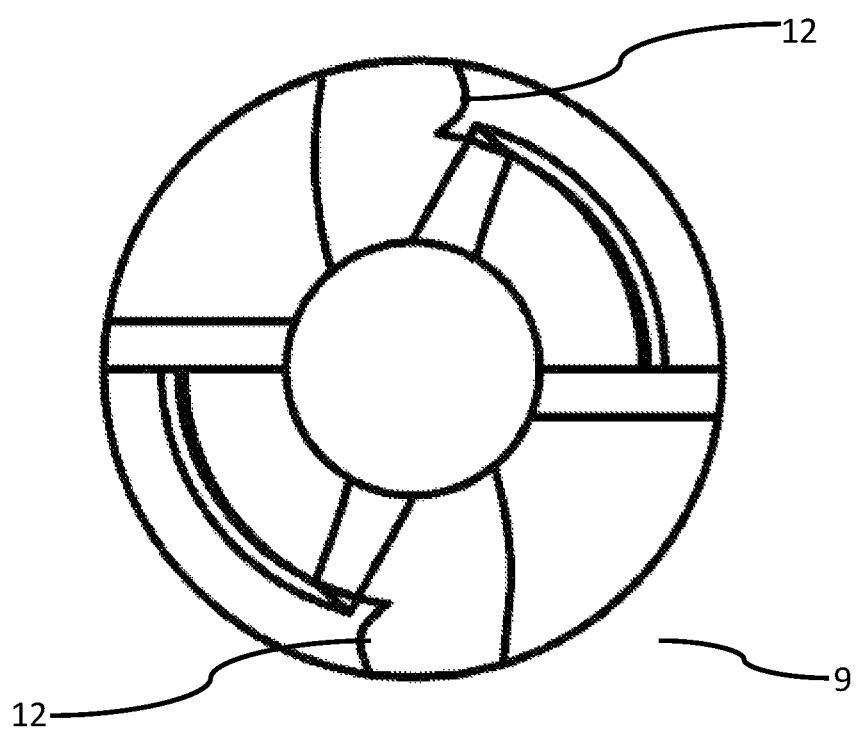
FIG. 15 Illustrates a front view of the cutting auger.
Figure 16:
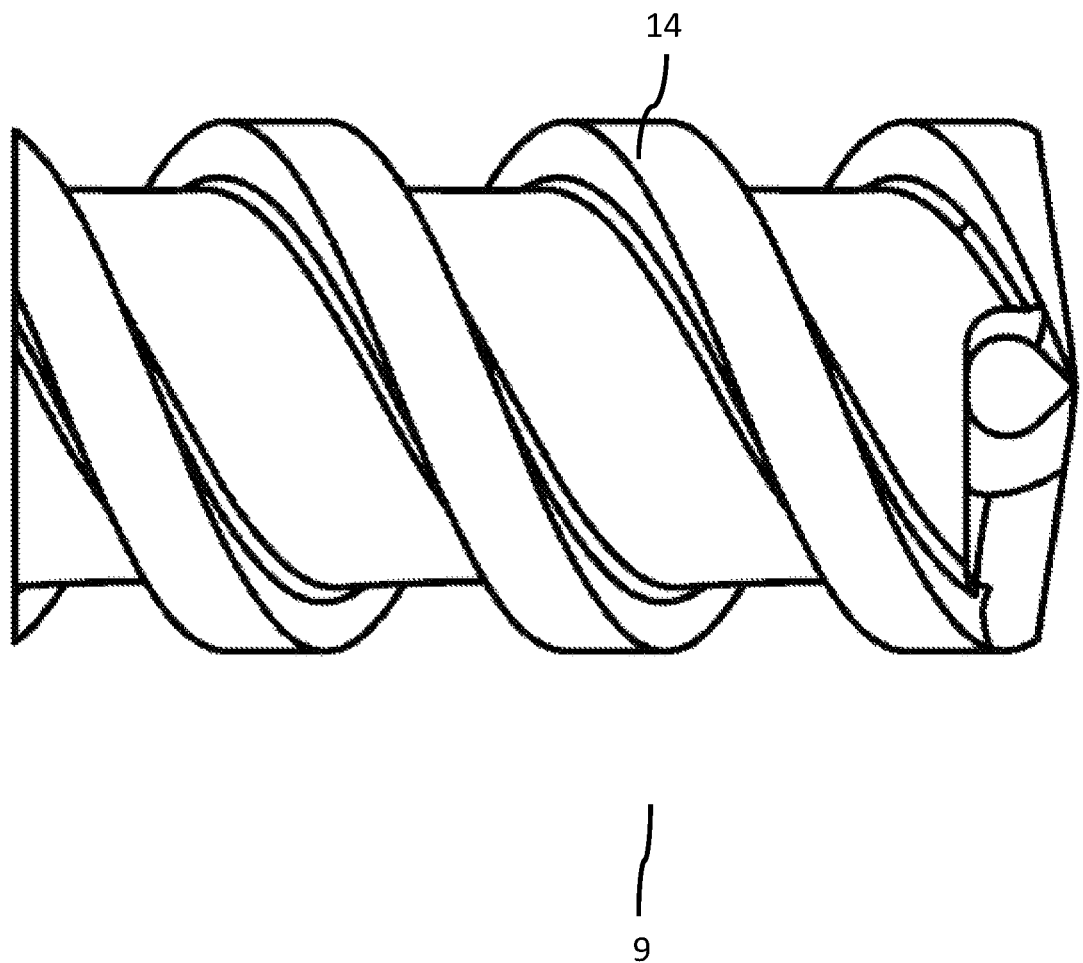
FIG. 16 Illustrates a side view of the cutting auger.

As illustrated in FIGS. 1-16, the subject invention discloses a plaque emulsifying, removal, and extraction device 1 for use in minimally invasive intravascular plaque removal from the inner walls 10 of blood vessels 13. The device 1 includes a catheter 2 containing a hollow elongated lumen with a distal end with a substantially cylindrical cutting auger 9 surrounded by a plaque extractor guide 3.

The plaque extractor guide 3 is a substantially cylindrical shape with an exterior surface 11. In other embodiments of the subject invention, the plaque extractor guide 3 may also be referred to as a plaque extractor shield, plaque extractor guard, plaque extractor cover, plaque extractor scoop or other terms known to those skilled in the art.

The plaque extractor guide 3 also contains a first channel 4 traversing subtantially one half of the cylindrical shape, with a proximal opening and a distal opening, wherein the first channel 4 is substantially crescent shaped. In embodiments of the subject invention, the first channel 4 of the plaque extractor guide 3 may be substantially crescent shaped, crescentoid shaped, c-shaped, oval, circular, half-moon shaped, sickle shaped, menicus shaped, or other shapes known to those skilled in the art. The substantially crescent shaped first channel 4 may be a width of 30% to 45% of the diameter of the plaque extractor guide 3.

The plaque extractor guide 3 also includes a second channel 5 traversing subtantially the other half of the cylindrical shape with a proximal opening and a distal opening. The second channel 5 is substantially circular. The proximal end of the second channel 5 is substantially aligned with the distal opening of the catheter 2. The distal end of the second channel 5 of the plaque extractor guide 3 contains a slot 6 and a scoop 7. The scoop 7 includes a substantially smooth, curved surface extending outward, and a distal blunt edge 8. The slot 6 contains a substantially smooth, curved surface extending inward. The substantially smooth surfaces of the exterior surface 11, scoop 7, edge 8, and slot 6 of the plaque extractor guide 3 cannot cut or tear the inner walls 10 of blood vessels 13 during operation of the device 1.

The substantially cylindrical cutting auger 9 contained with the second channel 5 of the plaque extractor guide 3, contains a proximal end and a distal end. In embodiments of the subject invention, the cutting auger 9 may also be referred to as an extraction wire, a screw auger, plaque extractor, plaque emulsifier, plaque macerator, plaque pulverizer, plaque separator, plaque remover, or other terms known to those skilled in the art. The proximal end of the cutting auger 9 is substantially aligned with the distal opening of the catheter 2. The cutting auger 9 contains helical ridges 14, and at least two occlusive material cutting edges 12 on the distal end, extending outwardly from the distal opening of the second channel 5 of the plaque extractor guide 3. Due to the size and configuration of the cutting edges 12, they cannot reach the inner walls 10 of blood vessels 13 during operation of the device 1, preventing any cutting or tearing of the inner walls 10 of blood vessels 13, by the cutting edges 12.

The cutting auger 9 may be implemented with a hole axially through the center, for delivery of the plaque extractor 3 over a guide wire, or with a solid center for applications not requiring a guide wire.

In embodiments of the subject invention, to insert the device 1, a small incision may be made on the patient, near the blood vessel 13 to be treated, or femoral, brachial, or radial access may be used with the device 1 being directed to the occlusion site to be treated using guide sheaths or guide catheters.

During delivery (or navigation) of the device 1 to the occlusion site the plaque extractor guide 3 and the cutting auger 9 may be configured to each independently rotate in the same direction, thereby reducing friction, to move axially within the guide sheaths, guide catheters, and blood vessels until the occlusion site is reached.

Once the device 1 has reached the occlusion site to be treated, the plaque extractor guide 3 and the cutting auger 9 are configured to each independently rotate in opposite directions during plaque extraction and move axially inside the vessel 13 to engage the occlusive material. The cutting auger 9 may rotate at a rate equal to, faster, or slower than the plaque extractor guide 3. Once in contact with the occlusion, or when restricted by the inner diameter of a blood vessel 13, the plaque extractor guide 3 rotates around its center axis. The plaque extractor guide 3 rotation may be concentric with the inner vessel wall 10.

The cutting auger 9 and catheter 2 rotate in an eccentric rotation with regard to the plaque extractor guide 3 and the inner vessel wall 10. Due to this eccentric rotation, the cutting auger 9 and catheter 2 move axially in an eccentric path within the vessel, substantially covering the entire cross-section of the extractor guide 3. The plaque extractor guide 3 and the cutting auger 9 are locked to maintain the same relative axial positions to one another.

The slot 6 and the scoop 7 of the plaque extractor guide 3 shaves and scoops the occlusive material located outside the eccentric path of the eccentrically rotating cutter 9 into the side cutting edges 12 of the cutting auger 9 for emulsification into reduced particles. The movement of the slot 6 and the scoop 7 of the plaque extractor guide 3 does not pierce or cut the vessel wall 10. Any occlusive material located within the eccentric path of the eccentrically rotating cutter auger 9 is emulsified into reduced particles by the distal cutting edges 12.

During the plaque emulsification process, laminar blood flow 15 within the blood vessel 13 is not stopped. Blood continues to flow 15 distally through the substantially crescent shaped first channel 4 of the plaque extractor guide 3. A portion of the blood flows 15 around and into the device 1. The mixture of emulsified occlusive material and blood flows 15 in a proximal direction into the catheter 2 lumen through the cutting auger 9, while the remainder of the blood continues to flow 15 downstream. This blood flow 15 substantially maintains internal blood pressure downstream within the vessel and reduces any increase in internal blood pressure within the vessel due to insertion and operation of the device within the vessel.

In an additional embodiment of the subject invention, the first crescent shaped channel 4 may be accomplished with an inflatable and deflatable balloon structure. In this embodiment, as the plaque extractor guide 3 and the cutting auger 9 are being delivered to or removed from the occlusion material site, the balloon structure is deflated to minimize the overall diameter of the extractor guide 3 and allow a smaller incision on the patient and a smaller diameter guide catheter to be used to access the occluded vessel.

The invention claimed is:

1. A device configured to remove occlusive material from a vessel, comprising:

a catheter with a hollow elongated lumen, a proximal opening, and a distal opening;

a plaque extractor guide on the distal opening of the catheter, wherein the plaque extractor guide comprises a substantially cylindrical shape with an exterior surface;

wherein the plaque extractor guide comprises a first channel traversing substantially one half of the cylindrical shape, with a proximal opening and a distal opening, wherein the first channel is substantially crescent shaped, further wherein the plaque extractor guide comprises a second channel traversing substantially the other half of the cylindrical shape with a proximal opening and a distal opening, wherein the second channel is substantially circular, further wherein the proximal end of the second channel is substantially aligned with the distal opening of the catheter;

wherein the distal end of the second channel of the plaque extractor guide comprises a slot and a scoop, wherein the scoop comprises a substantially smooth, curved surface extending outward, and a distal blunt edge, and the slot comprises a substantially smooth, curved surface extending inward;

a substantially cylindrical cutting auger comprising helical shaped edges is contained within the second channel of the plaque extractor guide, wherein the cutting auger comprises a proximal end and a distal end, wherein the proximal end of the cutting auger is substantially aligned with the distal opening of the catheter;

wherein the helical shaped edges of the cutting auger are sharp and there are at least two occlusive material cutting edges on the distal end of the cutting auger extending outwardly from the distal opening of the second channel of the plaque extractor guide;

wherein the plaque extractor guide and the cutting auger are configured to each independently rotate in opposite directions during plaque extraction and move axially inside the vessel to engage the occlusive material;

wherein the plaque extractor guide and the cutting auger are configured to each independently rotate in the same direction during navigation to move axially within a guide sheath, guide catheter or blood vessel while the device is being delivered to the occlusive material site to minimize friction against the sheath, catheter and vessel walls;

wherein the plaque extractor guide rotates around its center axis, and the cutting auger and catheter rotate in an eccentric rotation and move axially in an eccentric path within the vessel;

wherein the slot and the scoop of the plaque extractor guide shaves and scoops the occlusive material located outside the eccentric path of the eccentrically rotating cutting auger into the occlusive material cutting edges of the cutting auger for emulsification into reduced particles such that the movement of the slot and the scoop of the plaque extractor guide does not pierce or cut the vessel wall;

wherein occlusive material located within the eccentric path of the eccentrically rotating cutting auger is emulsified into reduced particles by the occlusive material cutting edges;

wherein the cutting auger is configured to not contact the vessel wall;

wherein the mixture of emulsified occlusive material and blood flows in a proximal direction into the catheter lumen through the cutting auger; and wherein the remainder of the blood flowing distally through the substantially crescent shaped first channel of the plaque extractor guide, continues to flow downstream.

2. The device of claim 1, wherein the plaque extractor guide rotates at a rate of 20 rpm to 180 rpm.

3. The device of claim 1, wherein the cutting auger rotates at a rate of 60 rpm to 5000 rpm.

4. The device of claim 1, wherein the distal remaining blood flow through the first channel of the plaque extractor guide substantially maintains internal blood pressure within the vessel.

5. The device of claim 1, wherein the distal remaining blood flow through the first channel of the plaque extractor guide substantially reduces any increase in internal blood pressure within the vessel due to insertion and operation of the device within the vessel.

6. The device of claim 1, wherein the plaque extractor guide comprises a diameter of 1.5 to 8 millimeters.

7. The device of claim 1, wherein the rotational movement of the plaque extractor guide is independent from the rotational movement of the cutting auger, wherein the plaque extractor guide and the cutting auger are locked to maintain the same relative axial positions to one another.

8. The device of claim 1, wherein the cutting auger rotates at a rate faster than the plaque extractor guide.

9. The device of claim 1, wherein the substantially crescent shaped first channel comprises a width of 30% to 45% of the diameter of the plaque extractor guide.

10. The device of claim 1, wherein the substantially circular shaped second channel comprises a width of 30% to greater than 50% of the diameter of the plaque extractor guide.

11. The device of claim 1, wherein the substantially circular shaped second channel comprises a diameter that is 50% to 150% larger than width of the substantially crescent shaped first channel on the plaque extractor guide.

12. A device configured to remove occlusive material from a vessel, comprising: a catheter with a hollow elongated lumen, a proximal opening, and a distal opening;

a plaque extractor guide on the distal opening of the catheter, wherein the plaque extractor guide comprises a substantially cylindrical shape with an exterior surface;

wherein the plaque extractor guide comprises a first internal channel with a proximal opening and a distal opening;

further wherein the plaque extractor guide comprises a second channel with a proximal opening and a distal opening, wherein the proximal end of the second channel is substantially aligned with the distal opening of the catheter;

wherein the distal end of the second channel of the plaque extractor guide comprises a slot and a scoop, wherein the scoop comprises a substantially smooth, curved surface extending outward, and a distal blunt edge, and the slot comprises a substantially smooth, curved surface extending inward;

a substantially cylindrical cutting auger comprising helical shaped edges contained with the second channel of the plaque extractor guide, wherein the cutting auger comprises a proximal end and a distal end, wherein the proximal end of the cutting auger is substantially aligned with the distal opening of the catheter;

wherein the helical shaped edges of the cutting auger are sharp and there are at least two occlusive material cutting edges on a distal end of the cutting auger extending outwardly from the distal opening of the second channel of the plaque extractor guide;

wherein the plaque extractor guide and the cutting auger are configured to each independently rotate in opposite directions during plaque extraction and move axially inside the vessel to engage the occlusive material;

wherein the plaque extractor guide and the cutting auger are configured to each independently rotate in the same direction during navigation to move axially within a guide sheath, guide catheter or blood vessel while the device is being delivered to the occlusive material site to minimize friction against the sheath, catheter and vessel walls;

wherein the plaque extractor guide rotates around its center axis, and the cutting auger and catheter rotate in an eccentric rotation and move axially in an eccentric path within the vessel;

wherein the slot and the scoop of the plaque extractor guide shaves and scoops the occlusive material located outside the eccentric path of the eccentrically rotating cutting auger into the occlusive material cutting edges of the cutting auger for emulsification into reduced particles such that the movement of the slot and the scoop of the plaque extractor guide does not pierce or cut the vessel wall;

wherein occlusive material located within the eccentric path of the eccentrically rotating cutting auger is emulsified into reduced particles by the occlusive material cutting edges;

wherein the cutting auger is configured to not contact the vessel wall;

wherein blood continues to flow distally through the first channel of the plaque extractor guide; wherein a portion of the blood flows around and into the device: wherein the mixture of emulsified occlusive material and blood flows in a proximal direction into the catheter lumen through the cutting auger;

wherein the remainder of the blood continues to flow downstream.

13. The device of claim 12, wherein the plaque extractor guide rotates at a rate of 20 rpm to 180 rpm.

14. The device of claim 12, wherein the cutting auger rotates at a rate of 60 rpm to 5000 rpm.

15. The device of claim 12, wherein the remaining blood flow through the first channel of the plaque extractor guide substantially maintains internal blood pressure within the vessel.

16. The device of claim 12, wherein the remaining blood flow through the first channel of the plaque extractor guide substantially reduces any increase in internal blood pressure within the vessel due to insertion and operation of the device within the vessel.

17. The device of claim 12 wherein the plaque extractor guide comprises a diameter of 1.5 to 8 millimeters.

18. The device of claim 12, wherein the rotational movement of the plaque extractor guide is independent from the rotational movement of the cutting auger, wherein the plaque extractor guide and the cutting auger are locked to maintain the same relative axial positions to one another.

19. The device of claim 12, wherein the cutting auger rotates at a rate faster than the plaque extractor guide.

20. The device of claim 12, wherein the first channel comprises a width of 30% to 45% of the diameter of the plaque extractor guide.

* * * * *